United States Patent
Chung et al.

(10) Patent No.: US 12,414,907 B2
(45) Date of Patent: Sep. 16, 2025

(54) PEPTIDE HAVING HAIR GROWTH PROMOTING ACTIVITY AND USE THEREOF

(71) Applicant: CAREGEN CO., LTD., Anyang-si (KR)

(72) Inventors: Yongji Chung, Gunpo-si (KR); Eun Mi Kim, Yongin-si (KR); Eung Ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 805 days.

(21) Appl. No.: 17/629,236

(22) PCT Filed: Oct. 10, 2019

(86) PCT No.: PCT/KR2019/013268
§ 371 (c)(1),
(2) Date: Jan. 21, 2022

(87) PCT Pub. No.: WO2021/033832
PCT Pub. Date: Feb. 25, 2021

(65) Prior Publication Data
US 2022/0265538 A1    Aug. 25, 2022

(30) Foreign Application Priority Data

Aug. 20, 2019 (KR) .................. 10-2019-0101881

(51) Int. Cl.
| A61P 17/14 | (2006.01) |
| A61K 8/64 | (2006.01) |
| A61K 38/18 | (2006.01) |
| A61Q 7/00 | (2006.01) |

(52) U.S. Cl.
CPC ............. *A61K 8/64* (2013.01); *A61K 38/1841* (2013.01); *A61P 17/14* (2018.01); *A61Q 7/00* (2013.01)

(58) Field of Classification Search
None
See application file for complete search history.

(56) References Cited

U.S. PATENT DOCUMENTS

| 3,382,247 A | 5/1968 | Anthony et al. |
| 5,215,894 A | 6/1993 | Arison et al. |
| 5,516,891 A | 5/1996 | Siwruk et al. |
| 8,765,688 B2 | 7/2014 | Liebmann et al. |
| 9,295,629 B2 * | 3/2016 | Chung ............ C07K 7/08 |
| 10,112,978 B2 | 10/2018 | Nakagami et al. |
| 10,344,061 B2 | 7/2019 | Chung et al. |
| 10,508,140 B2 | 12/2019 | Chung et al. |
| 10,568,828 B2 | 2/2020 | Chung et al. |

FOREIGN PATENT DOCUMENTS

| EP | 3418293 A1 | 12/2018 |
| KR | 10-2002-0005332 A | 1/2002 |
| KR | 10-2013-0015530 A | 2/2013 |
| KR | 10-2013-0032788 A | 4/2013 |
| KR | 10-2013-0083484 A | 7/2013 |
| KR | 10-2017-0055550 A | 5/2017 |
| KR | 10-2017-0097834 A | 8/2017 |
| KR | 10-2017-0098195 A | 8/2017 |
| KR | 10-2017-0105697 A | 9/2017 |
| WO | WO-2017142305 * | 8/2017 | ............. A61K 38/08 |
| WO | WO-2017142305 A1 * | 8/2017 | ............. A61K 38/08 |

OTHER PUBLICATIONS

Willis et al (https://www.abc.net.au/news/health/2018-04-04/hair-loss-balding-causes-and-treatments-explained/9597934). (Year: 2018).*
Notice of Allowance dated May 3, 2021, for Korean Application No. 10-2019-0101881, Jeong et al., "The peptide having activity and use thereof" (partial English translation) (7 pages).
Anonymous, "UPI000406C18A, UniParc," UniProt. <https://www.uniprot.org/uniparc/UPI000406C18A/entry>, retrieved on Feb. 21, 2023 (Jun. 2016) (1 page).
Extended European Search Report dated Mar. 7, 2023, for European Patent Application No. 19942044.9, applicant: Caregen Co., Ltd., (4 pages).
Madaan et al., "Review of hair follicle dermal papilla cells as in vitro screening model for hair growth," Int. J. Cosmet. Sci. 40(5):429-450 (Oct. 2018).

* cited by examiner

*Primary Examiner* — Celeste A Roney
(74) *Attorney, Agent, or Firm* — Clark & Elbing LLP

(57) ABSTRACT

Provided are a peptide having an activity of promoting hair generation and use thereof. In particular, provided are a peptide consisting of an amino acid sequence of SEQ ID NO: 1, a composition including the peptide for improving hair loss or promoting hair generation, and a pharmaceutical composition including the peptide for preventing or treating hair loss.

9 Claims, 3 Drawing Sheets

Specification includes a Sequence Listing.

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: peptide

<400> SEQUENCE: 1

Trp Gln Asn Met Arg Leu
1               5

<210> SEQ ID NO 2
<211> LENGTH: 21
<212> TYPE: DNA
<213> ORGANISM: Artificial Sequence
<220> FEATURE:
<223> OTHER INFORMATION: TGF beta-1 primer_forward

<400> SEQUENCE: 2
```

```
gccctggata ccaactattg c                                              21

<210> SEQ ID NO 3
<211> LENGTH: 21
<212> TYPE: DNA
<213> ORGANISM: Artificial Sequence
<220> FEATURE:
<223> OTHER INFORMATION: TGF beta-1 primer_reverse

<400> SEQUENCE: 3
tcagcacttg caggagtagc g                                              21

<210> SEQ ID NO 4
<211> LENGTH: 25
<212> TYPE: DNA
<213> ORGANISM: Artificial Sequence
<220> FEATURE:
<223> OTHER INFORMATION: GAPDH primer_forward

<400> SEQUENCE: 4
ggtgtgaacg gatttggccg tattg                                          25

<210> SEQ ID NO 5
<211> LENGTH: 25
<212> TYPE: DNA
<213> ORGANISM: Artificial Sequence
<220> FEATURE:
<223> OTHER INFORMATION: GAPDH primer_reverse

<400> SEQUENCE: 5
ccgttgaatt tgccgtgagt ggagt                                          25
```

PEPTIDE HAVING HAIR GROWTH PROMOTING ACTIVITY AND USE THEREOF

SEQUENCE LISTING

The instant application contains a Sequence Listing which has been submitted electronically in ASCII format and is hereby incorporated by reference in its entirety. Said ASCII copy, created on Jan. 20, 2022, is named 51401-030001_Sequence_Listing_1_20_22_ST25 and is 1,242 bytes in size.

TECHNICAL FIELD

The present disclosure relates to a peptide having an activity of promoting hair generation and use thereof.

BACKGROUND ART

As an aging society develops, the number of people suffering from hair loss is increase. Hair loss was previously a major concern for middle-aged men, but in recent years, an interest in hair loss prevention and hair generation is increasing among young people and women as well. Hair loss has been recognized as a series of aging phenomena, but it has been recently found that hair loss progresses due to various causes including stress, westernized eating habits, nutritional imbalance, and changes in social activities, along with genetic factors.

As drugs that exhibit hair generation effects and are approved by the US FDA, Minoxidil (6-amino-1,2-dihydro-1-hydroxy-2-imino-4-phenoxypyrimidine) (U.S. Pat. No. 3,382,247) and Finasteride (U.S. Pat. No. 5,215,894) are currently available. In the case of Minoxidil, it was developed as a vasodilator for the treatment of hypertension in the early 1970s. However, as a side effect of hirsutism was reported, it has been used as a hair generation promotor. Accordingly, phenomena of exhibiting effects of thickening the hair by thickened pores and increased diameter of the hair are shown. Also, in the case of finasteride, it was developed as a medicine for benign prostatic hyperplasia, but is currently used as a medicine for hair loss. Accordingly, phenomena of slowing the hair loss progress and exhibiting hair generation effects are shown.

However, Minoxidil had side effects reported such as weight gain, edema, dermatitis, and heart rate increase, and finasteride which requires continuous use had side effects such as sexual dysfunction in men and birth defects in pregnant women. Thus, the development of hair loss treatment without side effects is still in demand.

Under such technical background, various studies are in progress to improve hair loss through mechanisms including hormone control and metabolic control (KR 2002-0005332), but the study process is incomplete yet.

DESCRIPTION OF EMBODIMENTS

Technical Problem

An aspect of the present disclosure provides a peptide consisting of an amino acid sequence of SEQ ID NO: 1.

Another aspect of the present disclosure provides a cosmetic composition including the peptide for improving hair loss or promoting hair generation.

Another aspect of the present disclosure provides a pharmaceutical composition including the peptide for preventing or treating hair loss.

Other purposes and advantages of the present disclosure will become more obvious with the following detailed description, claims, and drawing. Contents not described herein will be sufficiently recognized and inferred by those skilled in the technical field of the present application or in a similar technical field therewith, and thus descriptions of such contents will be omitted.

Solution to Problem

Description and embodiments disclosed herein may also be applied to other descriptions and embodiments, respectively. That is, all combinations of various elements disclosed herein belong to the scope of the present disclosure. In addition, the scope of the present application is not construed to be limited by the detailed description provided below.

An aspect of the present disclosure provides a peptide consisting of an amino acid sequence of SEQ ID NO: 1.

The term "peptide" as used herein refers to a linear molecule in which amino acid residues bind to each other via a peptide linkage. The peptide may be prepared by chemical synthesis methods known in the art, particularly, solid-phase synthesis techniques (Merrifield, J. Amer. Chem. Soc. 85:2149-54 (1963); Stewart, et al., Solid Phase Peptide Synthesis, 2nd. ed., Pierce Chem. Co.: Rockford, 111 (1984)) or liquid-phase synthesis techniques (U.S. Pat. No. 5,516,891). The inventors of the present disclosure endeavored to develop a peptide having a biologically effective activity, and consequently established a peptide consisting of an amino acid sequence of SEQ ID NO: 1. Here, the biologically effective activity may include any one or more characteristics selected from: (a) promotion of an activity of hair follicle cells; (b) promotion of proliferation of hair follicle cells; (c) inhibition of apoptosis of hair follicle cells; and (d) inhibition of expression of Dickkopf-related protein (DKK-1) or transforming growth factor-beta 1 (TGF-β1). In this regard, the peptide may be used for the purpose of improving hair loss or promoting hair generation, or for preventing or treating hair loss.

To obtain chemical stability, enhanced pharmacological properties (e.g., half-life, absorbency, titer, efficacy, etc.), modified specificity (e.g., broad spectrum of biological activity), and reduced antigenicity, an N-terminus or a C-terminus of the peptide may be bound to a protecting group. In an embodiment, the N-terminus of the peptide may be bound to any one protecting group selected from the group consisting of an acetyl group, a fluoreonylmethoxycarbonyl group, a formyl group, a palmitoyl group, a myristyl group, a stearyl group, a butoxycarbonyl group (Boc), an allyloxycarbonyl group (Alloc), and polyethylene glycol (PEG); and/or the C-terminus of the peptide may be bound to any one protecting group selected from the group consisting of an amino group (—$NH_2$), a tertiary alkyl group, and an azide group (—$NHNH_2$). In addition, the peptide may optionally further include an amino acid sequence that is prepared for a particular purpose to increase stability of a target sequence, a tag, a labeled residue, a half-life, or a peptide.

The term "stability" as used herein refers to storage stability (e.g., room temperature storage stability) as well as in vivo stability that protects the peptide from the attack of in vivo proteolytic enzymes.

Another aspect of the present disclosure provides: a cosmetic composition including, as an active ingredient, the peptide including the amino acid sequence of SEQ ID NO: 1; a pharmaceutical composition including, as an active ingredient, the peptide including the amino acid sequence of SEQ ID NO: 1; and use of the peptide including the amino acid sequence of SEQ ID NO: 1 to prepare a cosmetic or pharmaceutical composition or to be used as a cosmetic or pharmaceutical composition.

Another aspect of the present disclosure provides a cosmetic composition including the peptide for preventing hair loss or promoting hair generation.

Overlapping terms or elements with those already mentioned in the description of the peptide are the same as described above.

The term "improvement" as used herein refers to parameters associated with alleviation or treatment of the condition, and for example, refers to any action that at least reduce severity of a symptom.

The term "improvement of hair loss" as used herein comprehensively refers to a process of treating, alleviating, or relaxing the hair loss state, or effects of the process. For example, the improvement of hair loss may be construed as representing regeneration of hair follicle cells, restoration of activity of hair follicle cells, inhibition of apoptosis of hair follicle cells, or inhibition of expression of factors causing hair loss, such as DKK-1 and TGF-β1.

The term "promotion of hair generation" as used herein refers to any action that increases hair growth from hair follicle cells. For example, the promotion of hair generation may refer any action that increases the total amount of hair in terms of effects of promoting proliferation, activity, or growth of hair follicle cells.

A functional peptide in the art had disadvantages in that it was not effectively introduced into target tissues or cells due to the size of the peptide itself despite its effective biological activity, or it disappeared from the body in a short period of time due to a short half-life. Meanwhile, the cosmetic composition according to an embodiment includes, as an active ingredient, a peptide consisting of 10 or less amino acids, and thus the active ingredient may have high skin penetration rates. For example, when topically applied onto the skin, the hair loss may be effectively prevented while the hair generation may be promoted.

In an embodiment, the peptide showed effects of promoting proliferation of dermal papilla cells, promoting expression of a proliferation-related factor, promoting a proliferation mechanism, and inhibiting expression of a hair loss-related factor. In this regard, the peptide may be utilized as an active ingredient in the cosmetic composition for improving hair loss or promoting hair generation.

The cosmetic composition may include: a cosmetically effective amount of the peptide; and/or a cosmetically acceptable carrier, but embodiments of the present disclosure are not limited thereto.

The term "cosmetically effective amount" as used herein refers to an amount that is sufficient to attain efficacy of the cosmetic composition in the improvement of hair loss or the promotion of hair generation.

A weight ratio of the peptide and the cosmetically acceptable carrier may be, for example, in a range of about 500:1 to about 1:500, and in an embodiment, in a range of about 450:1 to about 1:450, about 400:1 to about 1:400, about 350:1 to about 1:350, about 300:1 to about 1:300, about 250:1 to about 1:250, about 200:1 to about 1:200, about 150:1 to about 1:150, about 100:1 to about 1:100, about 80:1 to about 1:80, about 60:1 to about 1:60, about 40:1 to about 1:40, about 20:1 to about 1:20, about 10:1 to about 1:10, about 8:1 to about 1:8, about 6:1 to about 1:6, about 4:1 to about 1:4, or about 2:1 to about 1:2, but embodiments of the present disclosure are not limited thereto.

The cosmetic composition may be prepared in any formulation type conventionally prepared in the art. For example, the cosmetic composition may be formulated into a solution, a suspension, an emulsion, a paste, a gel, a cream, a lotion, a powder, a soap, a surfactant-containing cleansing, an oil, a powder foundation, an emulsion foundation, a wax foundation, a spray, and the like, but embodiments of the present disclosure are not limited thereto. For example, the cosmetic composition may be prepared in the formulation of emollient lotion, nourishing lotion, nourishing cream, massage cream, essence, eye cream, cleansing cream, cleansing foam, cleansing water, mask pack, spray, or powder.

When the formulation of the cosmetic composition is a paste, a cream, or a gel, an animal oil, a plant oil, wax, paraffin, starch, tragacanth, a cellulose derivative, polyethylene glycol, silicone, bentonite, silica, talc, or zinc oxide may be used as a carrier component.

When the formulation of the cosmetic composition is a powder or a spray, lactose, talc, silica, aluminum hydroxide, calcium silicate, or a polyamide powder may be used as the carrier component. For example, in cases where the formulation is a spray, the spray may further include a propellant, such as chlorofluorohydrocarbon, propane/butane, or dimethyl ether.

In cases where the formulation is a solution or an emulsion, a solvent, a solubilizer, or an emulsifier may be used as the carrier component, and examples of the carrier component are water, ethanol, isopropanol, ethyl carbonate, ethyl acetate, benzyl alcohol, benzyl benzoate, propylene glycol, 1,3-butylglycol oil, glycerol fatty ester, polyethylene glycol, or fatty acid ester of sorbitan.

In cases where the formulation is a suspension, a liquid diluent (such as water, ethanol, or propylene glycol), a suspending agent (such as ethoxylated isostearyl alcohol, polyoxyethylene sorbitol ester, and polyoxyethylene sorbitan ester), microcrystalline cellulose, aluminum metahydroxide, bentonite, agar, or tragacanth may be used as the carrier component.

In cases where the formulation is a surfactant-containing cleansing, aliphatic alcohol sulfate, aliphatic alcohol ether sulfate, sulfosuccinate monoester, isethionate, an imidazolinium derivative, methyl taurate, sarcosinate, fatty acid amide ether sulfate, alkyl amido betaine, aliphatic alcohol, fatty acid glyceride, fatty acid diethanolamide, plant oil, a lanoline derivative, or ethoxylated glycerol fatty acid ester may be used as the carrier component.

The components included in the cosmetic composition may include, in addition to the peptide as an active ingredient and the carrier component, components that are commonly used in the cosmetic composition. For example, the components may include common auxiliary agents, such as an antioxidant, a stabilizer, a solubilizer, a vitamin, a pigment, and a flavor.

Another aspect of the present disclosure provides a method of improving hair loss or promoting hair generation, the method including applying the cosmetic composition onto the skin of a subject, wherein the cosmetic composition includes, as an active ingredient, the peptide consisting of the amino acid sequence of SEQ ID NO: 1.

Overlapping terms or elements with those already mentioned in the description of the cosmetic composition are the same as described above.

The terms "applying", "administering", and "coating" are used interchangeably, and may be construed as causing at least partial localization by the composition according to an embodiment onto a desired site, or arranging the composition according to an embodiment into a subject by the administration route.

Another aspect of the present disclosure provides a pharmaceutical composition for preventing or treating hair loss, the composition including the peptide as an active ingredient.

Overlapping terms or elements with those already mentioned in the description of the peptide are the same as described above.

The term "prevention" as used herein refers to any action that can inhibit or delay the onset of a disease by administration of the composition.

The term "treatment" as used herein refers to any form of treatment that provides, to a subject afflicted with or at risk of developing a disease, effects including improving conditions (e.g., one or more symptoms) of the subject, delaying progression of a disease, delaying onset of symptoms, or slowing progression of symptoms. That is, the terms "treatment" and "prevention" are not intended to mean cure or complete elimination of symptoms.

The term "subject" as used herein refers to a target in need of disease treatment, and more particularly, refers to a mammal including a human or a non-human primate, such as a mouse, a dog, a cat, a horse, and a cow.

The "hair loss" which is a target disease to be prevented or treated by using the pharmaceutical composition may refer to a state in which there is no hair in the area where hair should normally exist, and specifically, it may refer a state where hair (thick and dark hair) of the scalp falls out. Causes of hair loss are not limited, but examples thereof are various dietary habits and environmental influences including such as genetic causes, hormonal imbalance, mental stress, exposure to air pollution, and intake of processed foods. For example, examples of the hair loss are hereditary androgenic alopecia (baldness), alopecia areata, tinea capitis due to fungal infection, telogen alopecia, trichotillomania, hair generation disorders, and the like. In detail, examples of cicatricial alopecia that leaves a scar are lupus hair loss, folliculitis decalvans, lichen planopilaris, and hair loss by burn and trauma.

In an embodiment, the peptide showed effects of promoting proliferation or activity of hair follicle cells or inhibiting expression of a hair loss-related factor. In this regard, the peptide may be utilized as an active ingredient in the pharmaceutical composition for preventing or treating hair loss.

The pharmaceutical composition may include: a pharmaceutically effective amount of the peptide; and/or a pharmaceutically acceptable carrier, but embodiments of the present disclosure are not limited thereto.

The term "pharmaceutically effective amount" as used herein refers to an amount that is sufficient to attain efficacy of the pharmaceutical cosmetic composition in the prevention or treatment of hair loss.

A weight ratio of the peptide and the pharmaceutically acceptable carrier may be, for example, in a range of about 500:1 to about 1:500, and in an embodiment, in a range of about 450:1 to about 1:450, about 400:1 to about 1:400, about 350:1 to about 1:350, about 300:1 to about 1:300, about 250:1 to about 1:250, about 200:1 to about 1:200, about 150:1 to about 1:150, about 100:1 to about 1:100, about 80:1 to about 1:80, about 60:1 to about 1:60, about 40:1 to about 1:40, about 20:1 to about 1:20, about 10:1 to about 1:10, about 8:1 to about 1:8, about 6:1 to about 1:6, about 4:1 to about 1:4, or about 2:1 to about 1:2, but embodiments of the present disclosure are not limited thereto.

The pharmaceutically acceptable carrier may be conventionally used at the time of formulation, and examples thereof are lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but are not limited thereto. Suitable pharmaceutically acceptable carriers and agents are described in detail in Remington's Pharmaceutical Sciences (19th ed., 1995).

The pharmaceutical composition may further include, in addition to the ingredients above, a lubricant, a wetting agent, a sweetening agent, a flavoring agent, an emulsifier, a suspending agent, a preservative, and the like, but is not limited thereto.

The pharmaceutical composition may be administered orally or parenterally, and preferably parenterally. Examples of the parenteral administration are intramuscular, intravenous, subcutaneous, intraperitoneal, local, and transdermal injections, but are not limited thereto.

A dose of the pharmaceutical composition may be in a range of about 0.0001 microgram (ug) per day to about 1,000 ug per day, about 0.001 ug per day to about 1,000 ug per day, about 0.01 ug per day to about 1,000 ug per day, about 0.1 ug per day to about 1,000 ug per day, or about 1.0 ug per day to about 1,000 ug per day, but is not limited thereto. The dose may be prescribed in various ways depending on factors, such as the method of formulation, the manner of administration, the age, body weight, gender, and morbidity of a patient, the diet, the time of administration, the route of administration, the excretion rate, and the response sensitivity.

The pharmaceutical composition may be formulated into a unit dosage form or prepared in a multi-dose container by formulating a pharmaceutically acceptable carrier and/or excipient according to the method easily carried out by a person having ordinary skill in the art to which the present invention pertains.

Another aspect of the present disclosure provides a method of preventing or treating hair loss, the method including administering, to a subject, the pharmaceutical composition, wherein the pharmaceutical composition includes, as an active ingredient, the peptide consisting of the amino acid sequence of SEQ ID NO: 1.

Overlapping terms or elements with those already mentioned in the description of the pharmaceutical composition are the same as described above.

Another aspect of the present disclosure provides a food composition for preventing or treating hair loss, the composition including, as an active ingredient, the peptide consisting of the amino acid sequence of SEQ ID NO: 1.

Overlapping terms or elements with those already mentioned in the description of the peptide are the same as described above.

An amount of the peptide which is included as an active ingredient in the food composition may be appropriately selected without limitation depending on the type of food, desired use, and the like. For example, the peptide may be added in an amount of 0.01 wt % to about 15 wt % based on the total food weight. Also, for example, the health beverage composition may be added in a proportion of about 0.02 g to about 10 g, preferably about 0.3 g to about 1 g, based on 100 ml of the peptide.

Advantageous Effects of Disclosure

A peptide according to an aspect may be applied for improving, preventing, or treating hair loss by inhibiting expression of a hair loss-related factor (such as DKK-1 or TGF-β1).

A peptide according to an aspect may be applied for promoting hair generation or hair growth by promoting proliferation, growth, or activity of hair follicle cells.

Thus, a peptide according to an aspect may be included as an active ingredient in a cosmetic composition or a pharmaceutical composition for improving hair loss or promoting hair generation.

MODE OF DISCLOSURE

Hereinafter, the present disclosure will be described in detail with reference to Examples below. However, these Examples are provided for illustrative purposes only, and the scope of the present disclosure is not limited thereto.

EXAMPLE 1: SYNTHESIS OF PEPTIDE

A peptide having an amino acid sequence of SEQ ID NO: 1 of Table 1 was synthesized by using an automatic peptide synthesizer Milligen 9050 (Millipore, USA). Then, C18 reverse-phase high-performance liquid chromatography (HPLC) (Waters Associates, USA) was performed thereon to purely separate the synthesized peptide. Here, ACQUITY UPLC BEH300 C18 column (2.1 mm×100 mm, 1.7 μm, Waters Co, USA) was used.

TABLE 1

| Amino acid sequence | SEQ ID NO. |
|---|---|
| WQNMRL | 1 |

EXAMPLE 2: CONFIRMATION OF PROMOTING EFFECTS OF PEPTIDE ON PROLIFERATION OR ACTIVITY OF HAIR FOLLICLE CELLS

1. Confirmation of Promoting Effect of Dermal Papilla Cells on Proliferation

The promoting effect of the peptide consisting of the amino acid sequence of SEQ ID NO: 1 on the proliferation of hair follicle cells was to be confirmed. In detail, human hair follicle dermal papilla cells were seeded in a 96-well plate at a density of $5\times10^3$ cells/well, and cultured for 16 hours. The culture medium was replaced with a serum-free medium, and the peptide was added thereto at a concentration of 0.5 uM, 5 uM, or 50 uM, and the cells were cultured for 72 hours. Here, as a positive control group, 5 uM of Minoxidil which is used as a hair loss treatment was treated. Afterwards, an MTT method was performed to measure the cell proliferation. In detail, 4 ug/ml of 3-(4,5-dimethylthiazol-2-yl)-2,5-diphenyltetrazolium bromide (MTT) was treated, and 4 hours later, DMSO was treated thereon to dissolve formazan. Then, the absorbance at 560 nm was measured by using a spectrophotometer.

Figure 1:
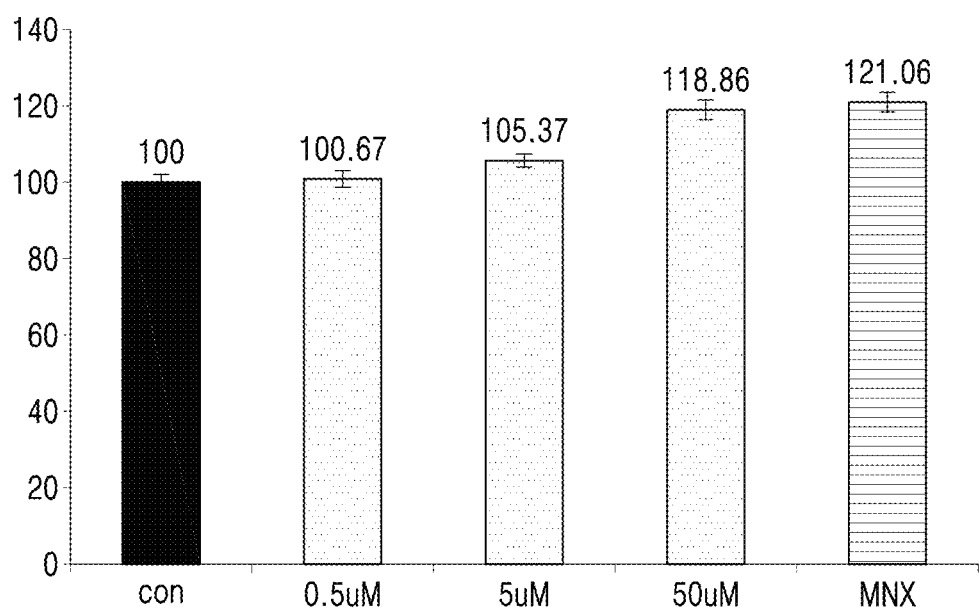
FIG. 1 shows a result confirming an effect of a peptide consisting of an amino acid sequence of SEQ ID NO: 1 on the promotion of proliferation of hair follicle cells.

Consequently, as shown in FIG. 1, it was confirmed that the peptide consisting of the amino acid sequence of SEQ ID NO: 1 promoted the proliferation of human dermal papilla cells.

2. Confirmation of Effect on Activation of Proliferation-Related Factors in Dermal Papilla Cells The effect of the peptide consisting of the amino acid sequence of SEQ ID NO: 1 on the activation of proliferation-related factors in hair follicle cells was to be confirmed. In detail, human dermal papilla cells were seeded in a 6-well plate at a density of $4\times10^5$ cells/well, and cultured for 16 hours. The culture medium was replaced with a serum-free medium, and the peptide was added thereto at a concentration of 0.5 uM, 5 uM, or 50 uM, and the cells were cultured for 30 minutes. Here, as a positive control group, 5 uM of Minoxidil was treated. Cell lysates were prepared by harvesting the cell, and then, western blotting was performed with respect to phosphorylated ERK and phosphorylated AKT by using p-ERK antibodies and p-AKT antibodies (Santacruz biotechnology, USA).

Figure 2:
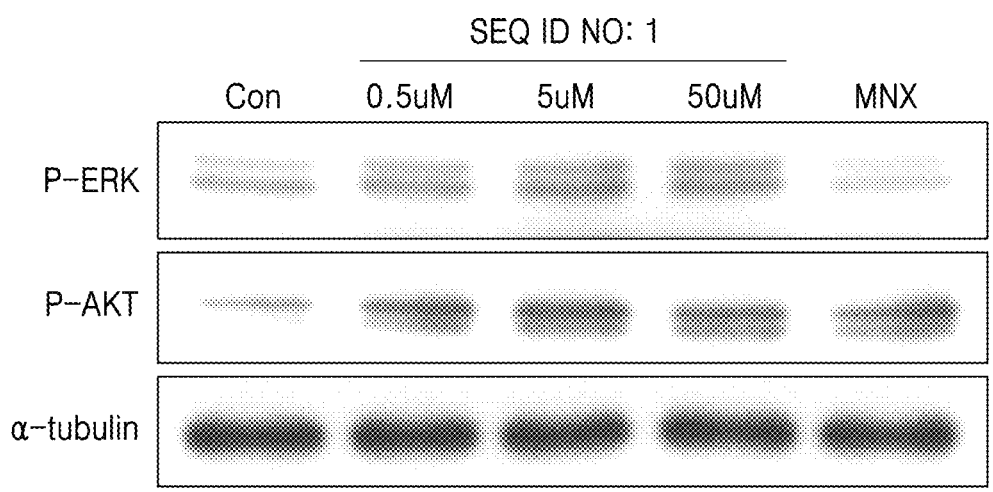
FIG. 2 shows a result confirming that phosphorylation, i.e., activation, of ERK and AKT which are factors related to proliferation of dermal papilla cells is induced, showing an effect of a peptide consisting of an amino acid sequence of SEQ ID NO: 1 on the promotion of proliferation of hair follicle cells.

Consequently, as shown in FIG. 2, it was confirmed that the phosphorylation of ERK and AKT, which are factors related to the proliferation of dermal papilla cells, was induced by the treatment with the peptide consisting of the amino acid sequence of SEQ ID NO: 1. As a result, it was confirmed that the factors related to the proliferation of dermal papilla cells were activated.

3. Confirmation of Activation Effect on Proliferation Mechanism of Dermal Papilla Cells The effect of the peptide consisting of the amino acid sequence of SEQ ID NO: 1 on the activation of a proliferation mechanism of hair follicle cells was to be confirmed. In detail, human dermal papilla cells were seeded in a 6-well plate at a density of $4\times10^5$ cells/well, and cultured for 16 hours. The culture medium was replaced with a serum-free medium, and the peptide was added thereto at a concentration of 0.5 uM, 5 uM, or 50 uM, and the cells were cultured for 24 hours. Here, as a positive control group, 5 uM of Minoxidil was treated. The cells were harvested and nuclear proteins thereof were isolated by using a nuclear protein extraction kit (Merck, USA). Then, western blotting was performed with respect to β-catenin which is a factor related to proliferation of the dermal papilla cells by using β-catenin antibodies (Santacruz biotechnology, USA).

Figure 3:
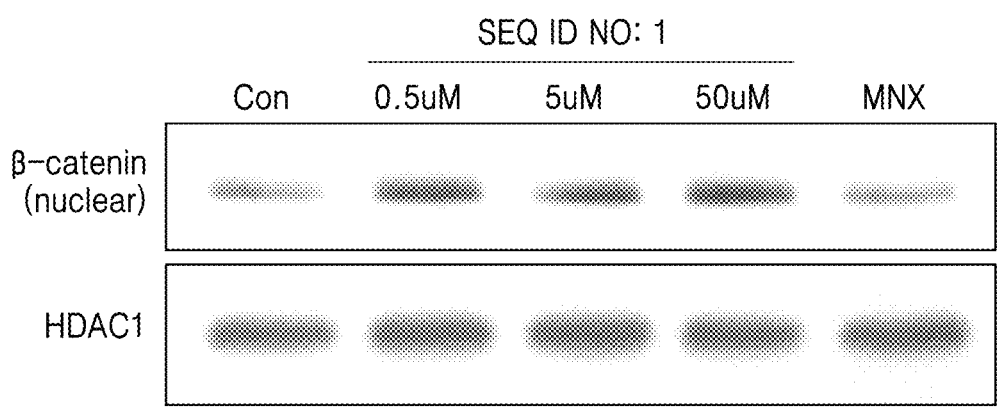
FIG. 3 shows a result confirming that β-catenin which is a factor related to proliferation of dermal papilla cells increases the movement from the cytoplasm to the nucleus, showing an effect of a peptide consisting of an amino acid sequence of SEQ ID NO: 1 on the promotion of proliferation of hair follicle cells.

Consequently, as shown in FIG. 3, it was confirmed that, by the treatment with the peptide consisting of the amino acid sequence of SEQ ID NO: 1, the movement of β-catenin from the cytoplasm to the nucleus was increased. As a result, it was confirmed that, due to the increased movement of β-catenin into the nucleus, β-catenin functioned as a transcription factor and the proliferation mechanism of the dermal papilla cells was promoted.

EXAMPLE 3: CONFIRMATION OF EFFECT OF PEPTIDE ON INHIBITION OF EXPRESSION OF HAIR LOSS-RELATED FACTORS 1.
Confirmation of Inhibitory Effect on Expression of DKK-1 in Dermal Papilla Cells The inhibitory effect of the peptide consisting of the amino acid sequence of SEQ ID NO: 1 on the expression of DKK-1, which is a hair loss-related factor, in hair follicle cells was to be confirmed. In detail, human dermal papilla cells were seeded in a 6-well plate at a density of $4 \times 10^5$ cells/well, and cultured for 16 hours. After the culture medium was replaced with a serum-free medium, dihydrotestosterone (DHT) as a stimulator was added thereto at a concentration of 10 ug/ml while peptide was added thereto at a concentration of 0.5 uM, 5 uM, or 50 uM. Then, the cells were cultured for 24 hours. The cells were harvested and nuclear proteins thereof were isolated by using a nuclear protein extraction kit. Then, western blotting was performed by using DKK-1 antibodies (Santacruz biotechnology, USA). Here, DHT is known as a hair loss hormone that increases the expression of DKK-1, which is a hair loss-inducible factor, by activating an androgen receptor.

Figure 4:
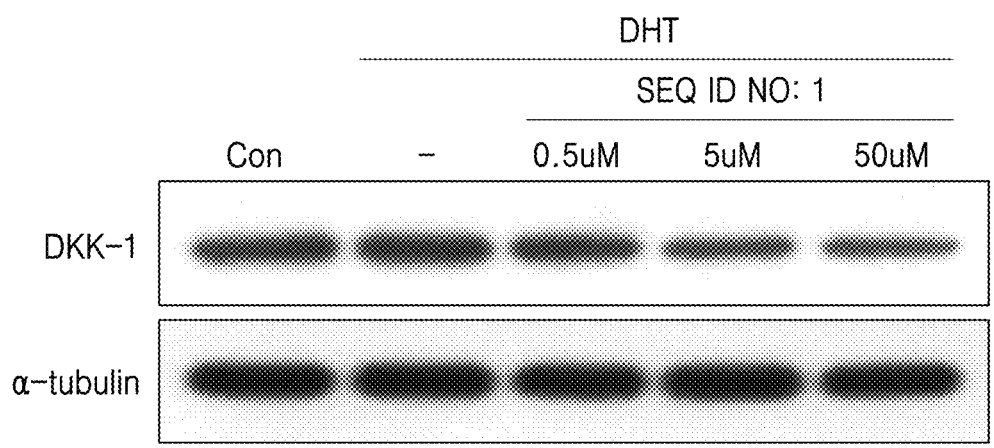
FIG. 4 shows a result confirming the inhibited expression pathway of DKK-1 by DHT treatment, showing an effect of the peptide consisting of the amino acid sequence of SEQ ID NO: 1 on the inhibition of expression of a hair loss-related factor in hair follicle cells.

Consequently, as shown in FIG. 4, it was confirmed that, by the treatment with DHT, the peptide consisting of the amino acid sequence of SEQ ID NO: 1 was able to inhibit the expression of DKK-1 which is a hair loss-inducible factor.

2. Confirmation of Inhibitory Effect on Expression of TGFβ-1 in Dermal Papilla Cells The inhibitory effect of the peptide consisting of the amino acid sequence of SEQ ID NO: 1 on the expression of TGFβ-1, which is a hair loss-related factor, in hair follicle cells was to be confirmed. In detail, human dermal papilla cells were seeded in a 6-well plate at a density of $4 \times 10^5$ cells/well, and cultured for 16 hours. The culture medium was replaced with a serum-free medium, and the peptide was added thereto at a concentration of 0.5 uM, 5 uM, or 50 uM, and the cells were cultured for 24 hours. Here, as a positive control group, 5 uM of Minoxidil was treated. After the cells were harvested, RNA was extracted therefrom and used for synthesis of cNDA by using a cDNA synthesis kit and PCR pre-mix. Then, PCR was performed by using primers of TGFβ-1 and GAPDH shown in Table 2. TGFβ-1, as an androgen-inducible factor in hair follicle cells, is known to be related to hair loss.

TABLE 2

| Primer | Sequence | (5'->3') | SEQ ID NO. |
|---|---|---|---|
| TGF-β1 | Foward | GCCCTGGATACCAACTATTGC | 2 |
|  | Reverse | TCAGCACTTGCAGGAGTAGCG | 3 |
| GAPDH | Foward | GGTGTGAACGGATTTGGCCGTATTG | 4 |
|  | Reverse | CCGTTGAATTTGCCGTGAGTGGAGT | 5 |

Figure 5:
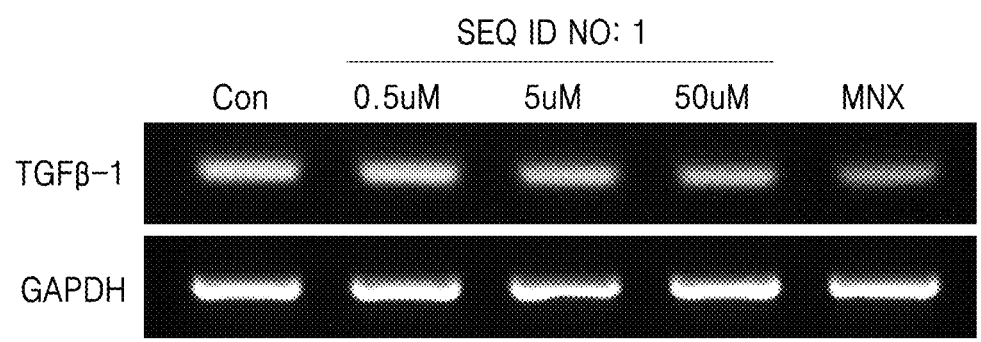
FIG. 5 shows a result confirming the inhibited expression pathway of TGF-β1, showing an effect of the peptide consisting of the amino acid sequence of SEQ ID NO: 1 on the inhibition of expression of a hair loss-related factor in hair follicle cells.

Consequently, as shown in FIG. 5, it was confirmed that the peptide consisting of the amino acid sequence of SEQ ID NO: 1 was able to inhibit the expression of TGFβ-1 which is known as a hair loss-inducible factor.

The foregoing descriptions are only for illustrating the present disclosure, and it will be apparent to a person having ordinary skill in the art to which the present invention pertains that the embodiments disclosed herein can be easily modified into other specific forms without changing the technical spirit or essential features. Therefore, it should be understood that Examples described herein are illustrative in all respects and are not limited.

The invention claimed is:

1. A peptide consisting of the amino acid sequence of SEQ ID NO: 1.

2. The peptide of claim 1, wherein the N-terminus of the peptide is bound to any one protecting group selected from the group consisting of an acetyl group, a fluoreonyl-methoxycarbonyl group, a formyl group, a palmitoyl group, a myristyl group, a stearyl group, a butoxycarbonyl group, an allyloxycarbonyl group, and polyethylene glycol (PEG).

3. The peptide of claim 1, wherein the C-terminus of the peptide is bound to any one protecting group selected from the group consisting of an amino group (—NH$_2$), a tertiary alkyl group, and a hydrazino an group (—NHNH$_2$).

4. The peptide of claim 1, wherein the peptide exhibits any one or more characteristics selected from the following:
 (a) promotion of activity of hair follicle cells;
 (b) promotion of proliferation of hair follicle cells;
 (c) inhibition of apoptosis of hair follicle cells; and
 (d) inhibition of expression of Dickkopf-related protein 1 (DKK-1) or transforming growth factor-beta 1 (TGF-β1).

5. A cosmetic composition for improving hair loss or promoting hair generation, the composition comprising the peptide of any one of claims 1 to 4 as an active ingredient.

6. A pharmaceutical composition for treating hair loss, the composition comprising the peptide of any one of claims 1 to 4 as an active ingredient.

7. A method of treating hair loss, the method comprising applying, to the skin of an individual, a peptide consisting of the amino acid sequence of SEQ ID NO: 1.

8. The method of claim 7, wherein the N-terminus of the peptide is bound to any one protecting group selected from the group consisting of an acetyl group, a fluoreonyl-methoxycarbonyl group, a formyl group, a palmitoyl group, a myristyl group, a stearyl group, a butoxycarbonyl group, an allyloxycarbonyl group, and polyethylene glycol (PEG).

9. The method of claim 7, wherein the C-terminus of the peptide is bound to any one protecting group selected from the group consisting of an amino group (—NH$_2$), a tertiary alkyl group, and a hydrazino group (—NHNH$_2$).

* * * * *